United States Patent
Woods et al.

(10) Patent No.: US 10,980,547 B2
(45) Date of Patent: Apr. 20, 2021

(54) CUTTING APPARATUS FOR BIOPROCESSING BONE

(71) Applicant: Ossium Health, Inc., San Francisco, CA (US)

(72) Inventors: Erik J. Woods, Carmel, IN (US); Brian H. Johnstone, Fishers, IN (US); Joseph Ingalls, Westfield, IN (US)

(73) Assignee: Ossium Health, Inc., San Francisco, CA (US)

( * ) Notice: Subject to any disclaimer, the term of this patent is extended or adjusted under 35 U.S.C. 154(b) by 0 days.

(21) Appl. No.: 17/079,309

(22) Filed: Oct. 23, 2020

(65) Prior Publication Data

US 2021/0037810 A1 Feb. 11, 2021

Related U.S. Application Data

(63) Continuation of application No. 16/409,808, filed on May 11, 2019.

(60) Provisional application No. 62/670,283, filed on May 11, 2018.

(51) Int. Cl.
*A61B 17/16* (2006.01)
*A01N 1/02* (2006.01)
*C12N 5/077* (2010.01)

(52) U.S. Cl.
CPC ............ *A61B 17/16* (2013.01); *A01N 1/0236* (2013.01); *A61B 17/1611* (2013.01); *C12N 5/0669* (2013.01); *C12N 2509/10* (2013.01)

(58) Field of Classification Search
CPC .... A01N 1/0236; A61B 17/16; A61B 17/1611
See application file for complete search history.

(56) References Cited

U.S. PATENT DOCUMENTS

| | | | |
|---|---|---|---|
| 1,002,826 A | | 9/1911 | Vilbiss |
| 1,604,695 A | * | 10/1926 | Hein .................. A61B 17/2812 606/83 |
| 2,472,103 A | * | 6/1949 | Giesen ............... A61B 17/8875 81/455 |

(Continued)

FOREIGN PATENT DOCUMENTS

EP 0244491 A1 11/1987

OTHER PUBLICATIONS

Ratchet Lever Arbor Presses, [retrieved on Mar. 4, 2021], Retrieved from the Internet: https://dakecorp.com/products/arbor-presses/ratchet-lever-arbor-press-1-1-2 (Year: 2021).*

(Continued)

*Primary Examiner* — Christian A Sevilla
(74) *Attorney, Agent, or Firm* — Wilson Sonsini Goodrich & Rosati

(57) ABSTRACT

A bone cutting assembly includes a manually actuated upper cutting element that carries a plurality of cutting blades configured to cut through frozen bone segments. A lower cutting element supports a bone segment to be cut and can include cutting blades aligned with the cutting blades of the upper cutting assembly. A pivoting linkage or a rack and pinion arrangement can be provided between the upper cutting element and a manually operated handle to provide sufficient mechanical advantage or leverage to allow an operator to manually cut through the bone.

19 Claims, 15 Drawing Sheets

(56) References Cited

U.S. PATENT DOCUMENTS

| | | | | |
|---|---|---|---|---|
| 3,507,284 | A | * | 4/1970 | Ravitz ................ A61B 17/1682 |
| | | | | 606/83 |
| 5,496,324 | A | * | 3/1996 | Barnes ................ A61B 17/175 |
| | | | | 409/179 |
| 5,766,177 | A | * | 6/1998 | Lucas-Dean ....... A61B 17/1611 |
| | | | | 606/170 |
| 9,265,565 | B2 | * | 2/2016 | Kerr ................... A61B 18/1442 |
| 2010/0063500 | A1 | * | 3/2010 | Muszala ............ A61B 18/1445 |
| | | | | 606/48 |
| 2019/0343112 | A1 | | 11/2019 | Woods et al. |

OTHER PUBLICATIONS

Dake 1-1/2 Model Ratchet Leverage Arbor Press with Handwheel and Counterweight, [retrieved on Mar. 4, 2021]. Retrieved from the Internet: https://www.amazon.com/Dake-1-1-Leverage-Handwheel-Counterweight/dp/B00DWB04 (Year: 2021).*

Model 1-1/2, 1/2B and 1-3/4 Ratchet Leverage Arbor Press Instruction and Parts list. Dake Corporation, [retrieved on Mar. 4, 2021]. Retrieved from the Internet: https://images-na.ssl-images-amazon.com/images/I/A1hpm91PFrL.pdf (Year: 2021).*

Brand: Huynh Thai Sau. 2 X S1211K Frozen Meat Bone Ice Cutting 300mm Reciprocating Saw Blade Tools Pack. For sale Amazon.com [https://www.amazon.com/S1211K-Frozen-Cutting-300mm-Reciprocating/dp/B07W4ZR9MR]. printed 2020.

Brand: SAVEMORE4U18. Automatic Bone Sawing Machine Frozen Meat Bone Cutter Food Cutting Machine. For sale Amazon.com [https://www.amazon.com/Automatic-Sawing-Machine-Frozen-Cutting/dp/B071352GWSG]. printed 2020.

Giraud et al.: Bone Cutting. Clin Phys Physiol Meas. 12(1):1-19. (1991) doi. 10.1088/0143-0815/12/1/001.

Kawamoto et al.: Preparation of thin frozen sections from nonfixed and undecalcified hard tissues using Kawamot's film method 2012. Methods Mol Biol . 1130:149-164 (2014) doi: 10.1007/978-1-62703-989-5_11.

* cited by examiner

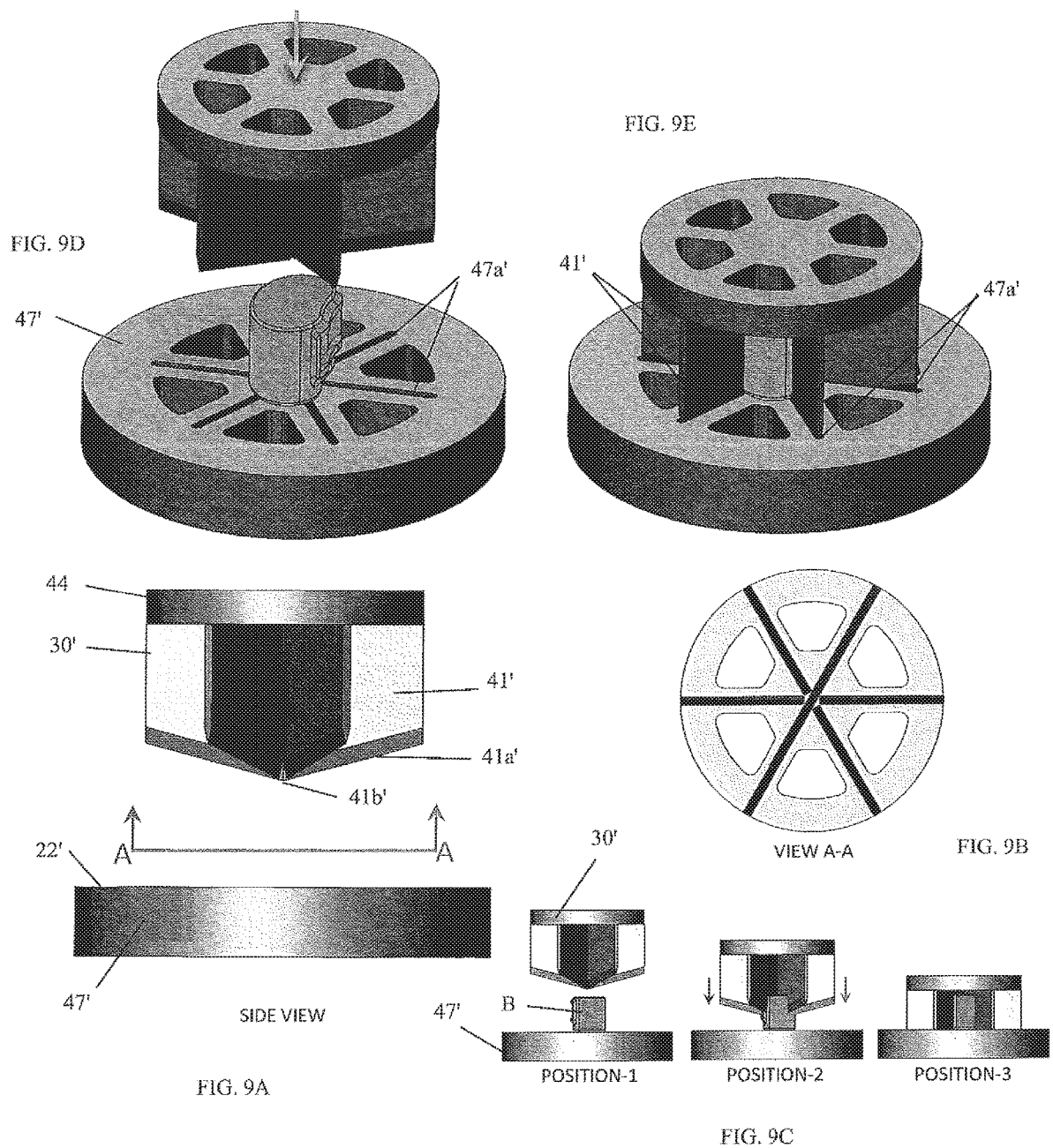

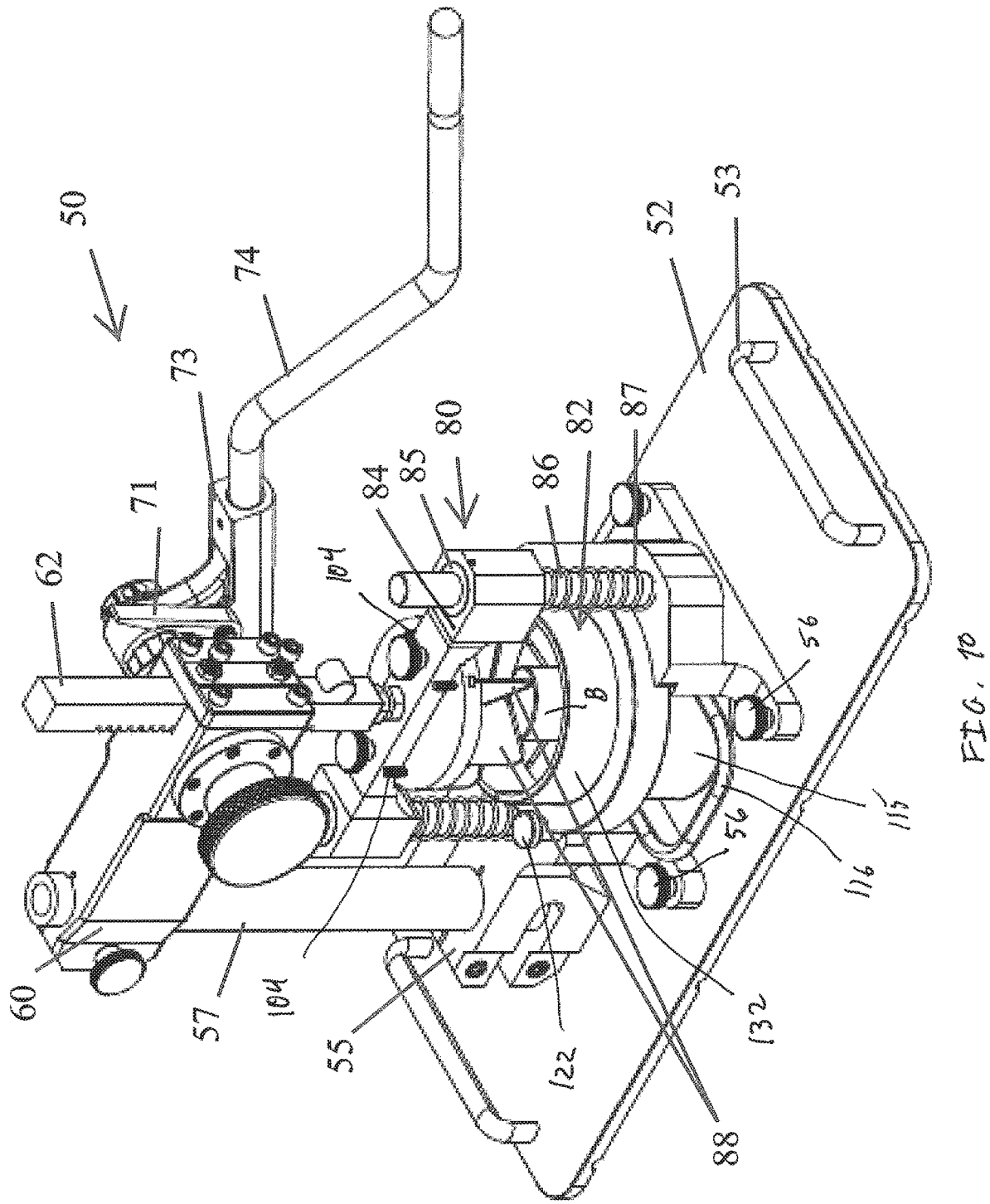

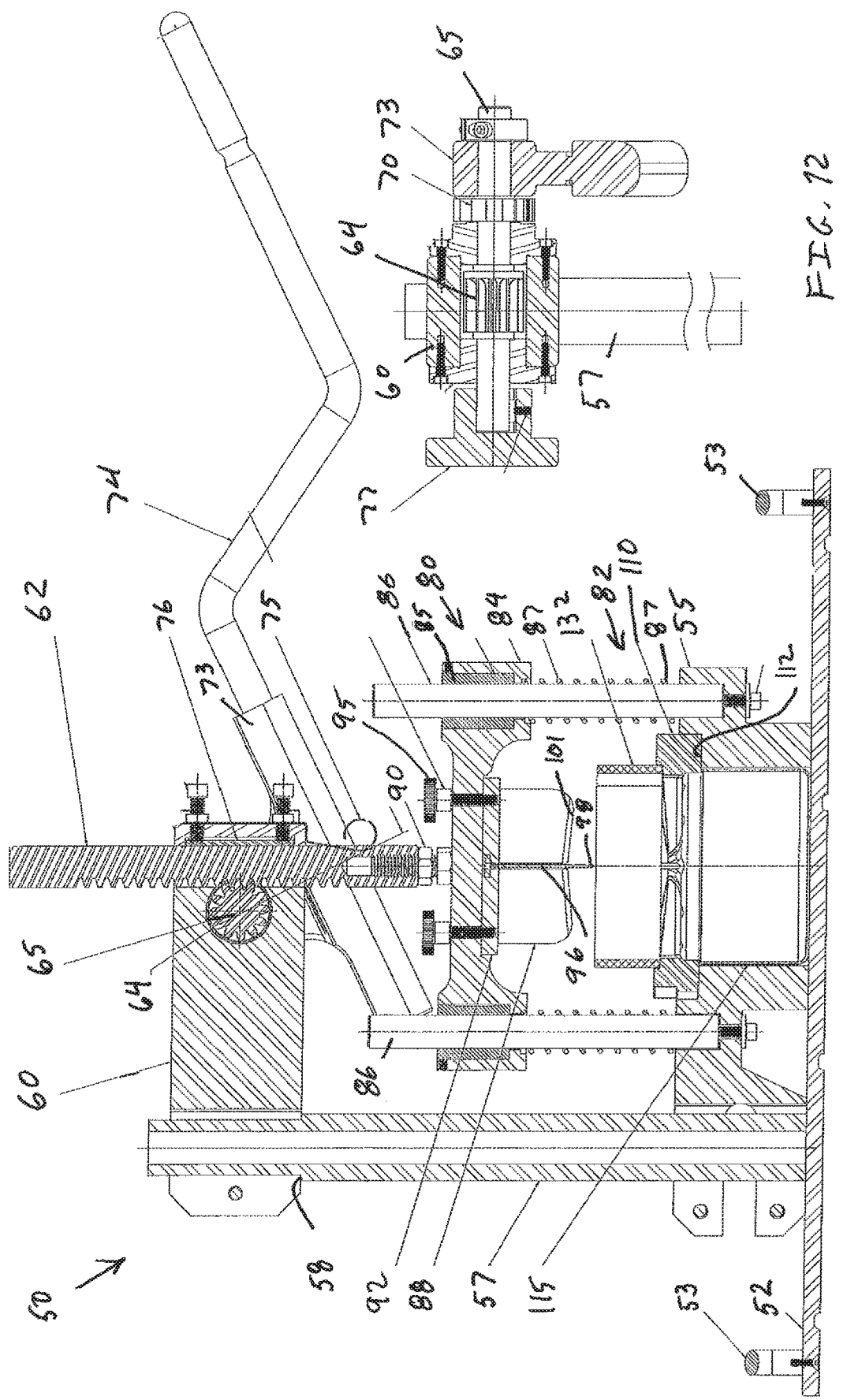

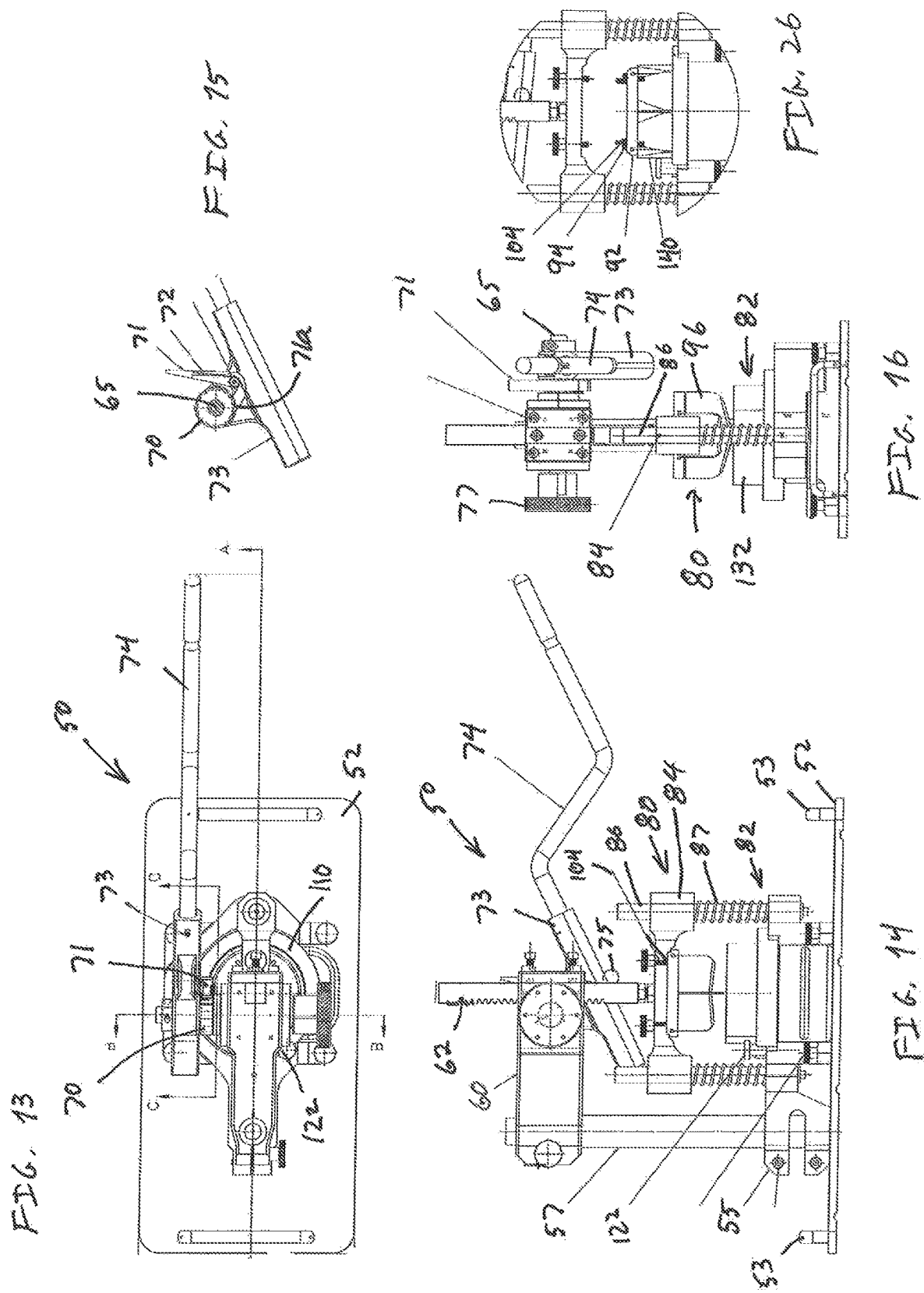

CUTTING APPARATUS FOR BIOPROCESSING BONE

PRIORITY CLAIM

This application is continuation of U.S. Ser. No. 16/409,808, filed May 11, 2019, which claims priority to U.S. 62/670,283, filed on May 11, 2018. The entire disclosure of each of which is incorporated herein by reference.

STATEMENT AS TO FEDERALLY SPONSORED RESEARCH

This invention was made with government support under contract number HL142418 awarded by the National Heart, Lung and Blood Institute. The government has certain rights in the invention.

BACKGROUND

The present disclosure concerns an apparatus useful for recovering live bone marrow.

Bone marrow for clinical purposes is harvested from HLA matched siblings or optimally matched unrelated donors (MUD). Other graft sources are mismatched haploidentical related or unrelated donors and umbilical cord blood (CB). When transplanted into patients with certain diseases, the hematopoietic stem cells (HSCs) in the donor bone marrow engraft in the patient and reconstitute immune and hematopoietic systems.

Bone marrow is also a source for mesenchymal stromal/stem cells (MSCs) which are self-renewing, multipotent progenitor cells with multilineage potential to differentiate into cell types of mesodermal origin, such as adipocytes, osteocytes, and chondrocytes. In addition, MSCs can migrate to sites of inflammation and exert potent immunosuppressive and anti-inflammatory effects through interactions between lymphocytes associated with both the innate and adaptive immune system.

Currently bone marrow is typically collected through a hole created in the outer bone with a trocar needle. A bone marrow aspiration needle is then introduced into the hole and a syringe is used to draw the marrow out of the bone. The syringes are then removed from the sterile field and connected to a collection bag containing anticoagulants. The marrow is pushed into the bag. This step is repeated many times, typically in both pelvic bones, and can often result in contamination of the aspirate.

Once recovered, bone marrow can be cryopreserved and banked for future use. This is typically done using a cryoprotectant agent (CPA) such as dimethyl sulfoxide (DMSO) with or without a carbohydrate, such as hydroxyethyl starch (HES), in a balanced electrolyte solution with or without a protein supplement, such as human or animal serum, platelet lysate, or albumin and with or without added growth factors. Cells are cooled slowly (−1° C. to −5° C./min) down to an intermediate, low sub-zero temperature and then transferred to final storage in vapor or liquid nitrogen.

Optimal cryopreservation techniques for bone marrow should be effective when applied to the whole tissue, with the idea that stem cells would be isolated following thawing, assuming adequate permeation of the cells to the CPA. Immediate cryopreservation of tissues is more practical than direct primary isolation of stem cells, which requires further processing and expense.

It is often optimal to cryopreserved whole bone to be subsequently processed for extraction of the bone marrow. To adequately cryopreserve bone for subsequent post thaw processing, the bone must be cooled very slowly (with cryoprotective agents) e.g. with cooling rates of −0.1° to −4.0° C. per min. However, to successfully recover live cells rapid warming is required (e.g. >50° C./min). While cooling rates can readily be applied in a slow manner, warming large volumes of bone quickly is problematic. Consequently, there is a need for an apparatus that can reduce the whole cryopreserved bone to smaller pieces that can then be placed into a warming medium immediately to allow rapid thaw.

SUMMARY OF THE DISCLOSURE

To enable cryopreservation of whole bone and facilitate subsequent processing of the bone, an apparatus is provided which can be used to process the bone and recover bone marrow to a cellular suspension prior to cryopreservation, or to enable the cryopreservation of whole bone to be subsequently processed. The apparatus allows either a fresh bone or a cryopreserved bone to be cut into pieces appropriately sized for further fresh processing or rapid thawing. In one embodiment, the apparatus is manually operated with a linkage arrangement or a lever arm and rack and pinion arrangement providing a mechanical advantage or leverage sufficient to cut through bone with only manual effort.

The present disclosure provides a bone cutting apparatus that comprises a lower cutting element configured to support a bone segment to be cut and an upper cutting element including a plurality of cutting blades facing the lower cutting element. A frame supports the upper cutting element above the lower cutting element for movement toward and away from the lower cutting element. The apparatus is provided with a manually operable handle and a force transmission mechanism connecting the handle to the upper cutting element to move the upper cutting element toward the lower cutting element with sufficient force to cut through the bone segment supported on the lower cutting element.

In one embodiment, the bone cutting apparatus includes upper and lower cutting elements, each with aligned cutting blades, in which the upper cutting element is pushed toward the stationary lower cutting element to cut through a bone segment positioned between the two elements. The upper cutting element is carried by a shaft that is connected to a linkage, that is in turn connected to a handle. The handle is pivotably mounted to the cutting apparatus so that pushing the handle downward pushes the upper cutting element downward with a mechanical advantage derived by the configuration of the handle and linkage.

In another embodiment, the upper cutting element is pushed by a handle applying force through a rack and pinion arrangement. A ratchet and pawl arrangement control the direction of movement of the rack that carries the upper cutting element. In this embodiment, the upper cutting element includes replaceable blades and a stationary lower cutting tray that supports the bone segment to be cut. A collection container is disposed beneath the lower cutting tray to receive the bone fragments at the completion of the cutting operation.

DESCRIPTION OF THE FIGURES

FIGS. 9A, 9B, 9C, 9D, and 9E are side, top and perspective views of another alternative cutting elements for use in the apparatus of FIG. 1, with FIG. 9C showing the cutting elements in different stages of operation.

FIG. 10 is a perspective view of a bone cutting apparatus according to another embodiment of the disclosure.

FIG. 11 is a side partial cross-sectional view of the apparatus shown in FIG. 10.

FIG. 12 is an enlarged cross-sectional view of a portion of the apparatus shown in FIG. 10.

FIG. 13 is a top view of the apparatus shown in FIG. 10.

FIG. 14 is a side view of the apparatus shown in FIG. 10.

FIG. 15 is an enlarged view of a portion of the apparatus shown in FIG. 10.

FIG. 16 is an end view of the apparatus shown in FIG. 10.

FIG. 26 is an enlarged end view of a portion of the apparatus of FIG. 10 shown with a blade assembly assist component.

DETAILED DESCRIPTION

Figure 1:
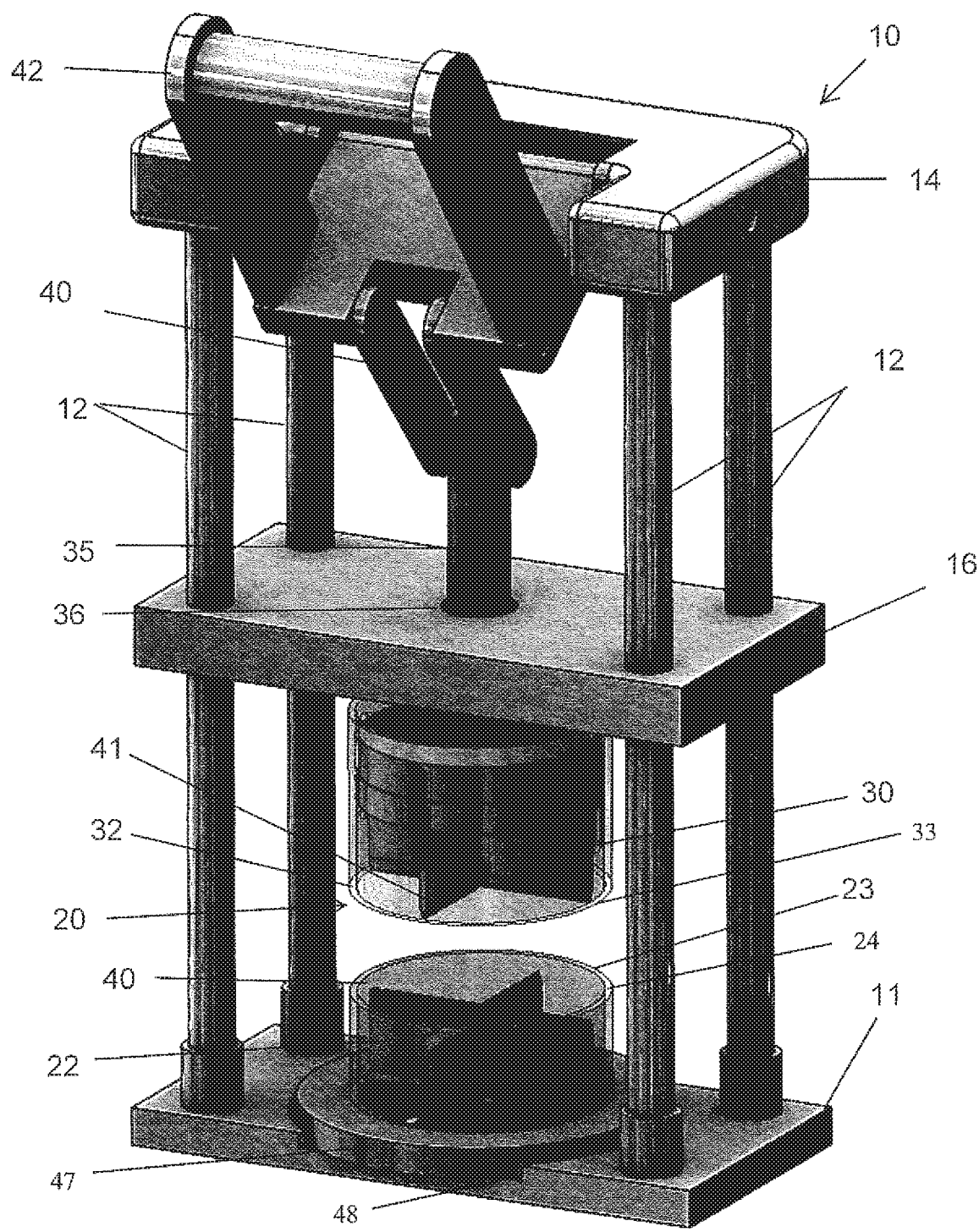
FIG. 1 is a perspective view of a bone cutting apparatus according to one embodiment of the present disclosure.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains.

Figure 2:
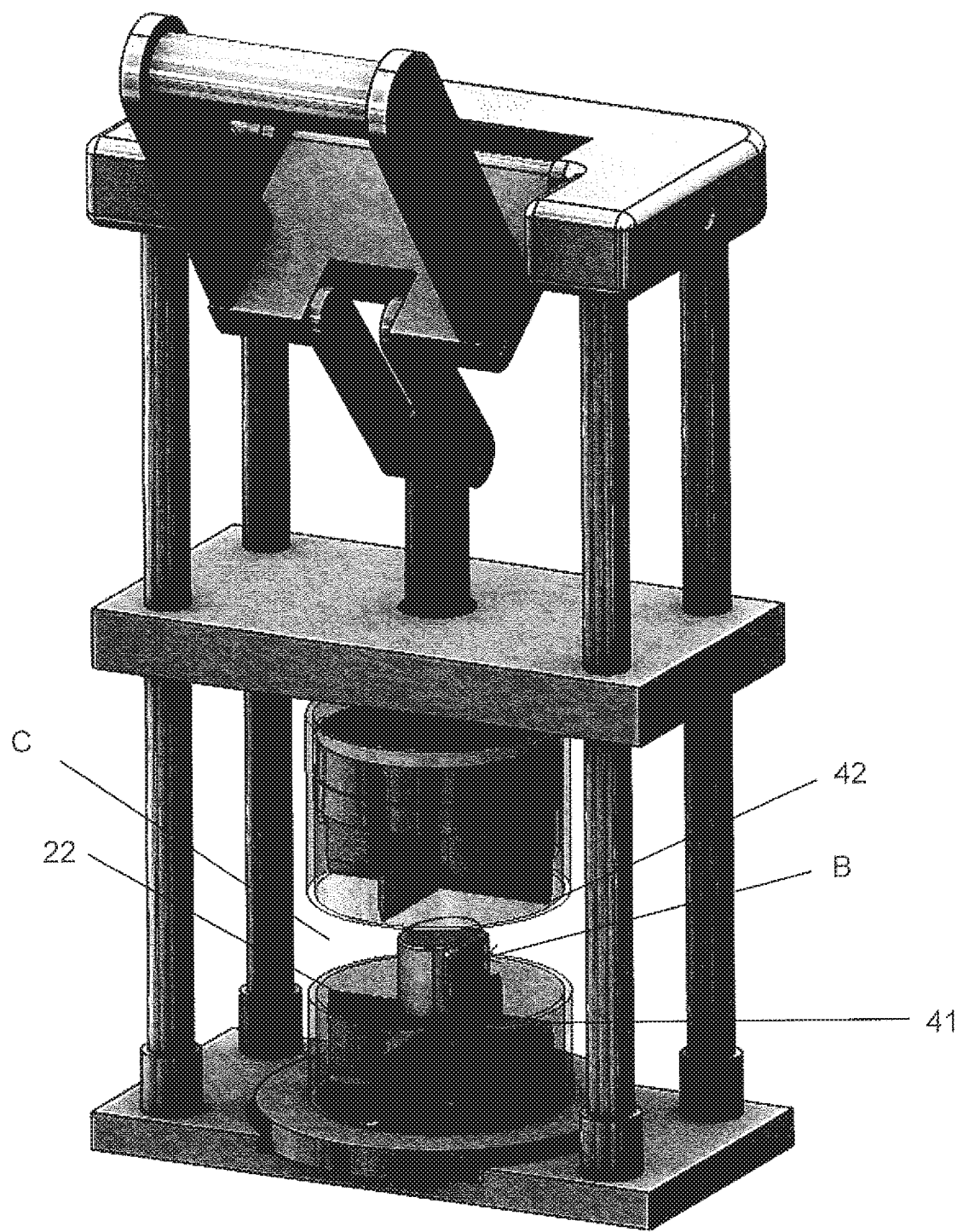
FIG. 2 is a perspective view of the apparatus of FIG. 1 shown in one stage of operation.
Figure 3:
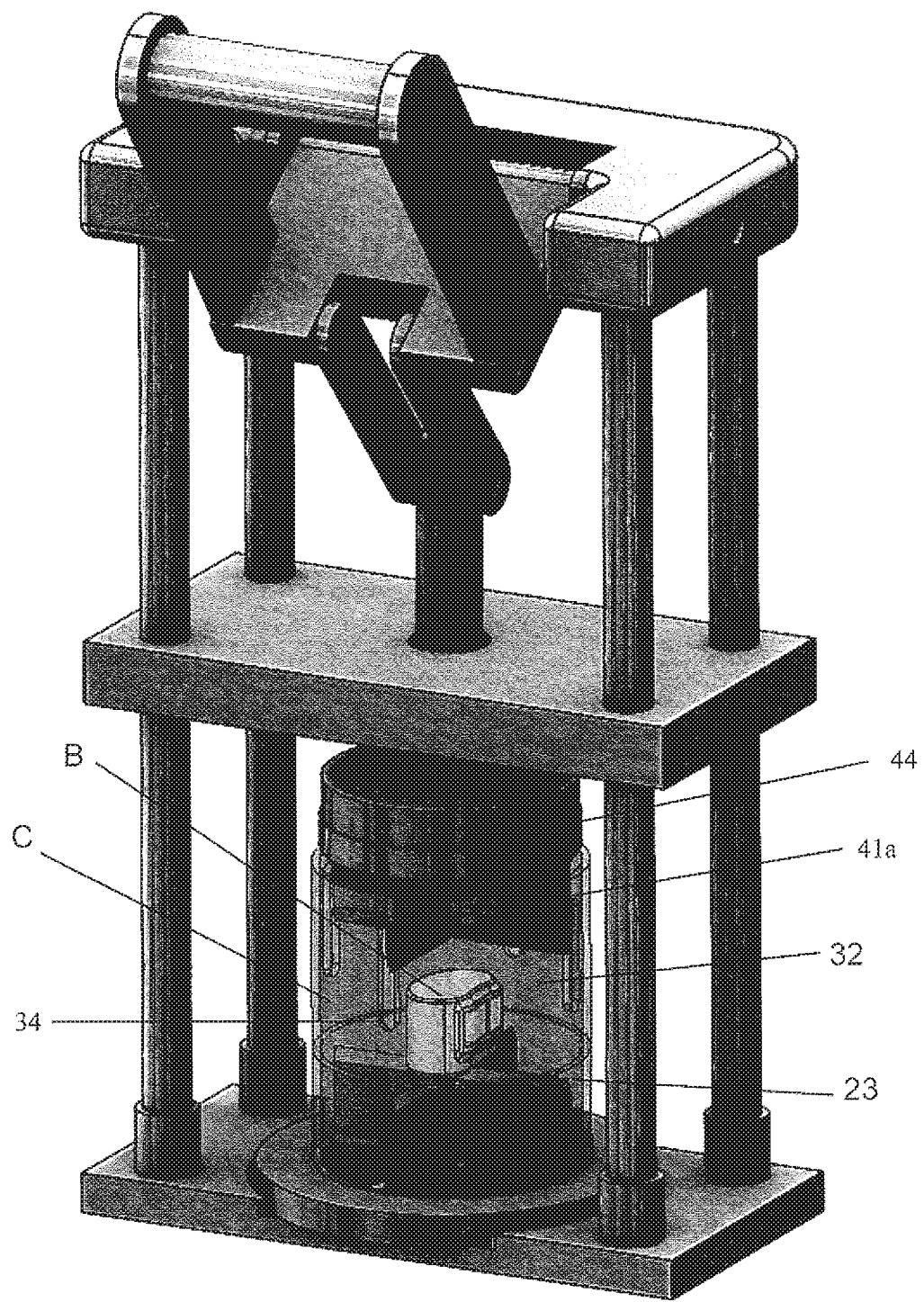
FIG. 3 is a perspective view of the apparatus of FIG. 1 shown in another stage of operation.

An apparatus 10 is provided, as shown in FIG. 1, for cutting a bone segment recovered from organ and tissue donors for subsequent processing. The apparatus includes a frame formed by a base plate 11 supporting four vertical columns 12. The frame also includes a top plate 14 is mounted on the four vertical columns and an intermediate plate 16 is mounted to the columns at a position between the base plate and top plate. A bone cutting assembly 20 is provided between the base plate 11 and the intermediate plate 16. The assembly 20 includes a lower cutter element 22 mounted on the base plate 11. The lower cutter element is surrounded by a shroud 23 arranged to contain fragments of a whole bone segment B (FIG. 2) generated in a cutting process. The assembly further includes a movable upper cutting element 30 that is also surrounded by a shroud 32. The two shrouds 23, 32 combine to form a chamber C to contain the whole bone segment during the cutting process, as shown in FIG. 3. In particular, the upper shroud 32 can be configured to slide downward toward the lower shroud 23 with the respective edges 24, 33 contacting each other, thereby closing the chamber C with the bone segment B inside. The edges 24, 33 can have complementary configurations so that one edge nests within the other edge to ensure proper alignment of the two shrouds.

The upper shroud 32 can include a plurality of vertical slots 34 that can receive a projection 41a on each of the cutting blades 41 of the upper cutting element 30. The projections 41a on the blades can thus guide the upper shroud 32 as it is moved from its uppermost position shown in FIG. 2 to its closed position shown in FIG. 3. In the closed position, the vertical slots 34 can then serve as a guide for the cutting blades 41 as the upper cutting element is moved from its uppermost position shown in FIG. 3 to its cutting position shown in FIG. 4. In one feature, the two shrouds are preferably formed of a transparent material, such as glass or certain plastics, to enable viewing of the whole bone segment prior to cutting and of the bone fragments after the cutting process.

Figure 4:
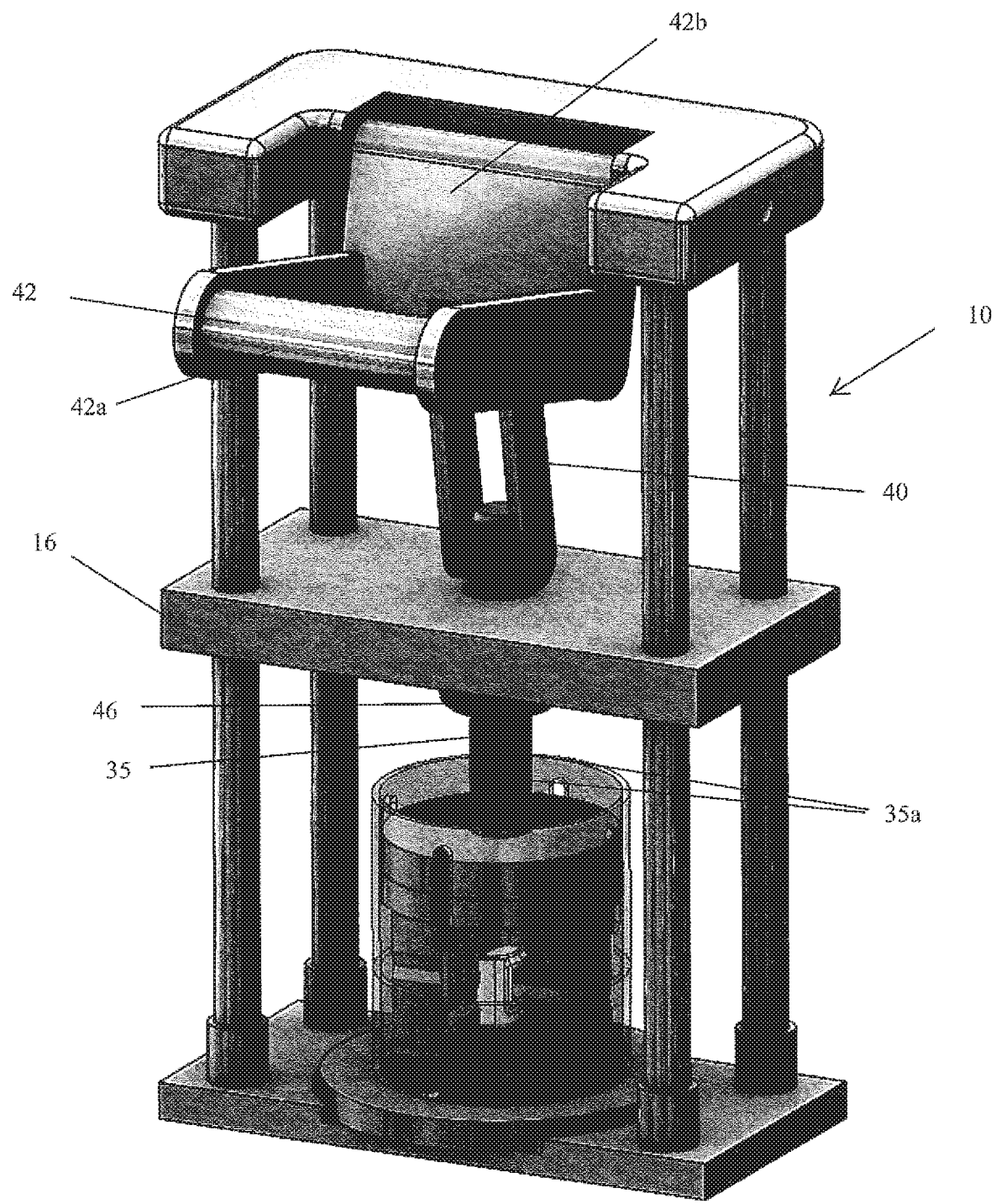
FIG. 4 is a perspective view of the apparatus of FIG. 1 shown in a further stage of operation.
Figure 5:
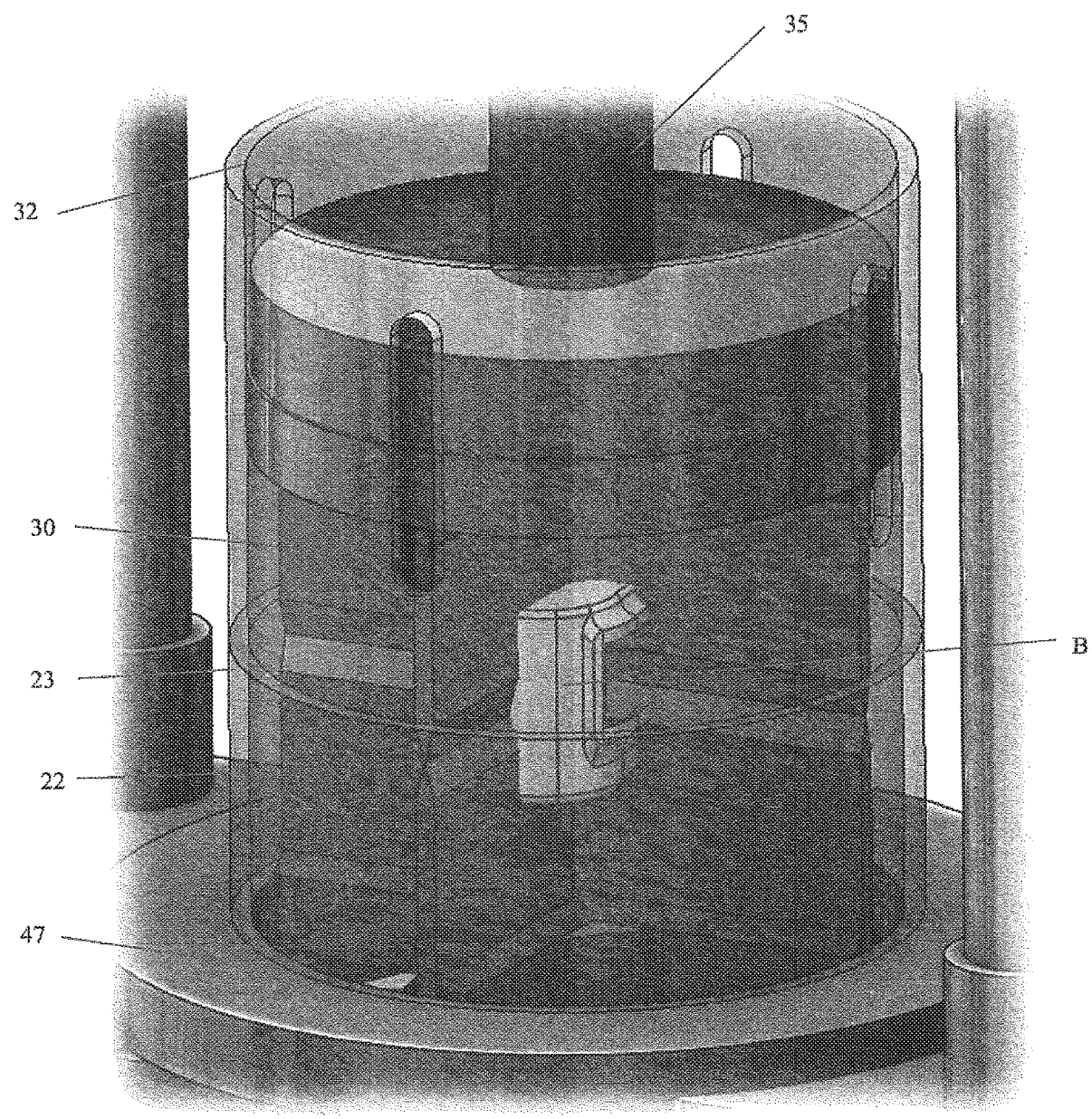
FIG. 5 is an enlarged view of the apparatus shown in FIG. 4.

The upper cutting element 30 is carried by a shaft 35 that extends through and is guided by a bore 36 in the intermediate plate 16. The upper end of the shaft 35 is pivotably connected to a linkage 40 that is pivotably connected to a handle 42. The handle 42 includes a hand grip portion 42a that is mounted or affixed at a generally perpendicular angle to a plate 42b, as best seen in FIG. 4. The plate 42b is pivotably mounted to the top plate 14 of the apparatus. The handle 42 is configured to be manually grasped and pivoted downward, which in turn pivots the linkage 40 about the end of the shaft in a direction opposite to the pivot direction of the handle, to thereby move the shaft 35, and thus the upper cutter element 30, downward toward the lower cutter element 22. The offset of the pivot connection of the linkage 40 to the handle 42 relative to the pivot connection of the handle 42 to the plate 16 provides a mechanical advantage that enables cutting through the bone segment B using only manual force. As shown in FIG. 2, the bone segment B is placed on top of the lower cutter element within the chamber C defined by the two shrouds 23, 32. The upper cutter element 30 is pressed into the bone segment to cut the segment into the shapes and dimensions set by the blades 40, 41 of the two cutter elements 22, 30, as depicted in FIG. 4.

The upper cutting element 30 can include a piston body 44 (FIG. 3) to which the cutting blades 41 are mounted. The cutting blades 41 can be separate blades mounted to the piston body or can be part of a cutting blade component. The piston body 44 can be engaged to the lower end of the shaft 35 in a conventional manner, such as by a threaded engagement. A bushing 46 (FIG. 4) can be affixed or mounted to the underside of the intermediate plate 16 to provide a bearing or sliding interface for the shaft 35. The shaft 35 may be provided with vertical splines 35a along the length of the shaft that engage mating vertical grooves (not shown) within the inner circumference of the bushing 46 to prevent rotation of the piston body 44 and cutting blades 41 during a cutting operation.

The lower cutter element 22 can include a base 47 onto which the cutting blades 40 are mounted or affixed. As with the cutting blades 41, the cutting blades 40 can be individually mounted to the base 47 or can be part of a cutting blade component. The base 47 is configured to be seated within a cavity or recess 48 defined in the bottom plate 11, as shown in FIG. 1. In this way, the lower cutting element 22 can be interchangeable or replaceable. The base 47 and recess 48 can include an alignment feature, such as a notch and complementary projection (not shown) to ensure a particular orientation of the cutting blades 40, and in particular to ensure that the cutting blades 40 are aligned with their counterpart cutting blades 41 in the upper cutting element 30. The splines 35a of the shaft 35 can include one spline that is larger than the others to mate with a correspondingly deeper groove in the bushing to align the upper cutter element 30. The key in the alignment features is that the cutting edges of the upper blades 41 are in direct alignment with the cutting edges of the lower blades 40 to properly cut through the bone segment B as the upper cutter element 30 is pushed toward the lower cutter element 22.

Figure 6A:
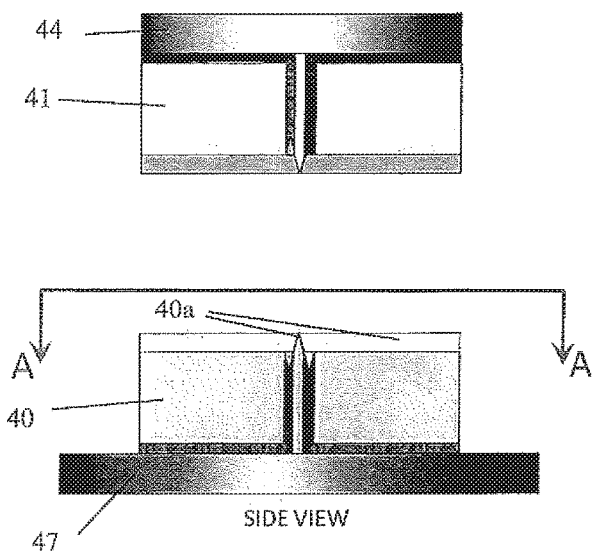
FIGS. 6A, 6B are side and top views of cutting elements for use in the apparatus of FIG. 1.
Figure 6B:
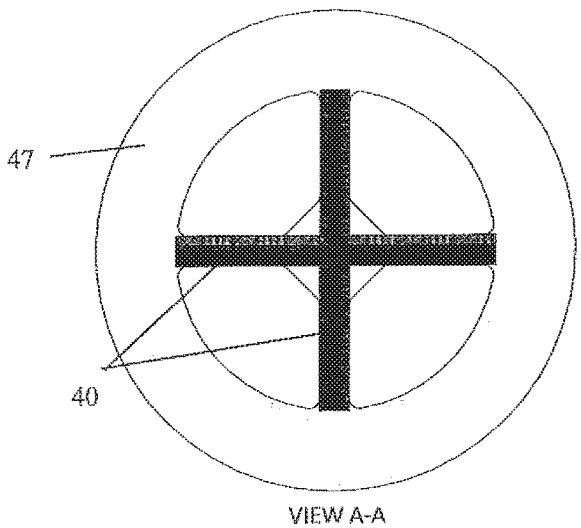
Figure 7A:
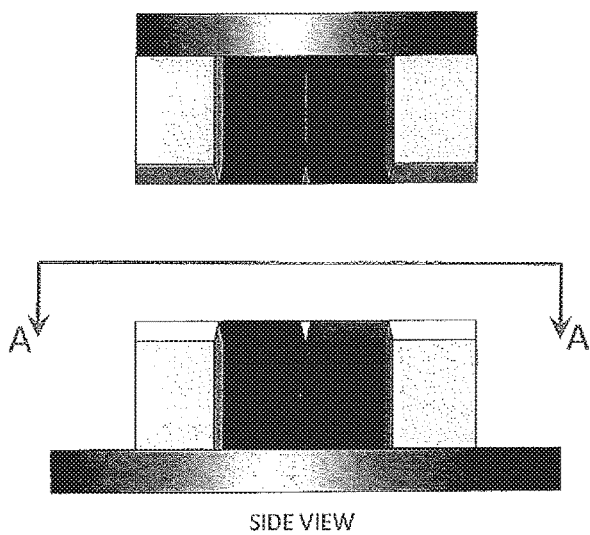
FIGS. 7A, 7B are side and top view of alternative cutting elements for use in the apparatus of FIG. 1.
Figure 7B:
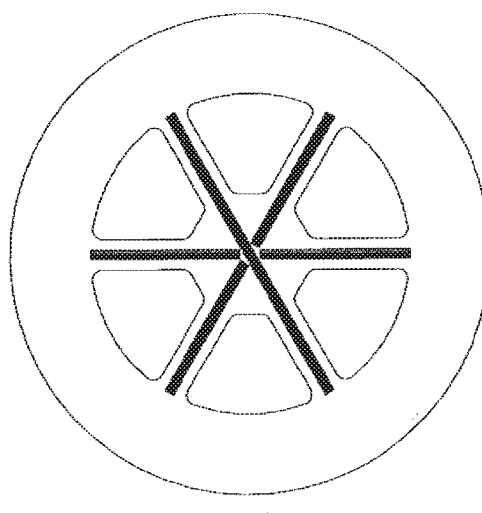
Figure 8A:
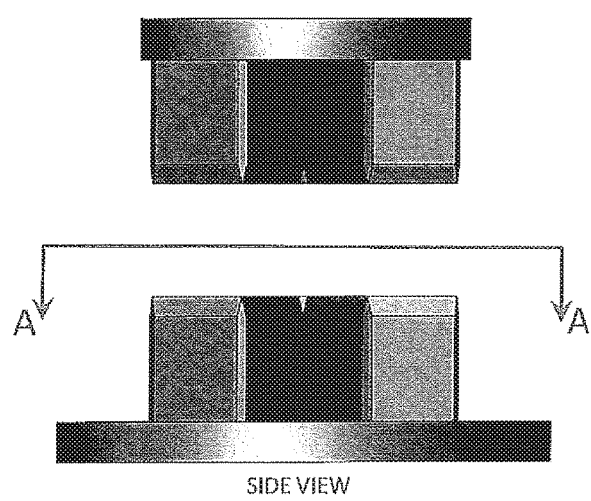
FIGS. 8A, 8B are side and top view of further alternative cutting elements for use in the apparatus of FIG. 1.
Figure 8B:
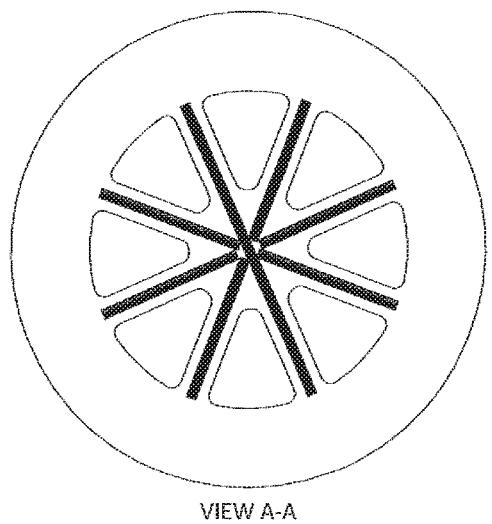

Several different configurations of cutting blades 40, 41 may be incorporated into the respective lower and upper cutter elements 22, 30. In one embodiment, four blades defining a "+" configuration can be provided as shown in FIGS. 6A, 6B. The cutting edges of the lower and upper cutting blades can have the configuration of the cutting edge 40a shown in FIG. 6A in which the blade is angled on both sides of the blade to a sharp edge and in which the edge 40a is linear and generally perpendicular to the vertical cutting direction. FIGS. 7a, 7b show an embodiment with six cutting blades having the same cutting edge configuration as the cutting edge 40a in FIG. 6A. FIGS. 8A, 8B show an embodiment with eight cutting blades having the same cutting edge configuration as the cutting edge 40a in FIG. 6A.

In an alternative embodiment shown in FIGS. 9A-9E, the lower cutting element 22' only includes the base 47' and does not include the cutting blades 40 of the previous embodiments. In this alternative embodiment, the upper cutting element 30' includes cutting blades 41' that have an angled cutting edge 41a'. The angled cutting edges 41a' of all of the cutting blades 41' converge at a central point 41b' that can facilitate the initial entry of the upper cutter element 30' into the bone segment, as depicted in FIG. 9C. In order to ensure a solid cut completely through the bone segment B, the base 47' of the lower cutter element 22' includes a plurality of slots 47a' that correspond with and are aligned with the cutting blades 41' of the upper cutter element 30. When the upper cutter element has been pushed through the bone segment B, the blades 41' penetrate the slots 47a' so that the entire angled edge 41a' (FIG. 9A) of the blades are within the slots, as in "Position 3" in FIG. 9C.

In specific embodiments, the upper and lower cutter elements can have a combined cutting height of about 2.5-3.0 inches in order to cut through bone segments B of the same height. The cutting blades can have a thickness of about 0.12 inches, tapering to a sharp point. In the embodiment of FIGS. 9A-9E, the angled cutting edges can be angled at about 15° relative to the horizontal.

Figure 17:
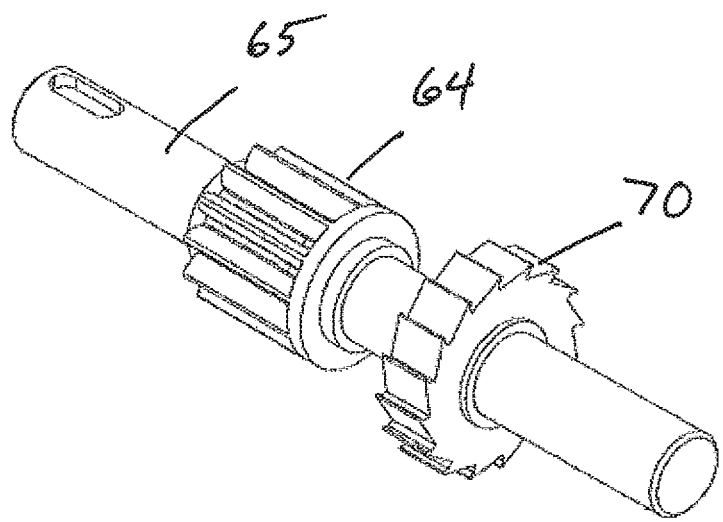
FIG. 17 is an enlarged perspective view of a component of the apparatus shown in FIG. 10.
Figure 20:
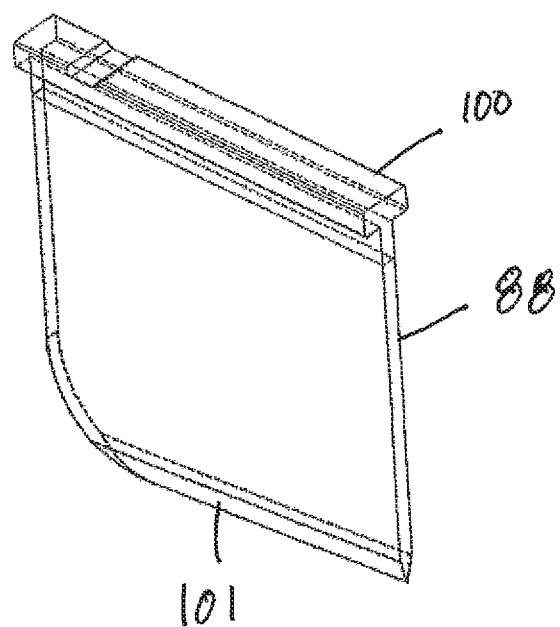
FIG. 20 is an enlarged perspective view of a cutting blade for use in the upper cutting element shown in FIGS. 18-19.

A bone cutting apparatus 50 according to another embodiment of the disclosure is shown in FIGS. 10-26. As shown in FIG. 10, the apparatus 50 includes a mounting plate 52 with handles 53 that allow the apparatus to be carried to different locations in a sterile bone processing facility. A base 55 is mounted to the mounting plate 52 by thumb screws 56 to permit ready disassembly and assembly of the apparatus. A post 57 is mounted to the base 55 to extend vertically above the plate 52. The post 57 defines a shoulder 58 (FIG. 11) on which is mounted a pinion mount 60. The pinion mount 60 supports a rack 62 for vertical movement relative to the plate 52. As shown in FIG. 11, the rack 62 engages a pinion gear 64 that is formed on a pinion shaft 65 (FIG. 17) so that rotation of the pinion gear 64 produces vertical movement of the rack 62. A rack spring 75 and a rack bearing 76 provide a lateral force to hold the rack 62 in toothed engagement with the pinion gear 64.

The pinion shaft 65 includes a ratchet gear 70 that is engaged by a pawl 71, as shown in FIGS. 12, 13, 15. A torsion spring 72 biases the claw 71a of the pawl 71 into engagement with the ratchet gear to hold the ratchet gear 70 and thus the pinion shaft 65 against rotation in one direction, while permitting rotation in the opposite direction. Thus, as viewed in FIG. 11, the ratchet gear and pawl are configured to permit rotation of the shaft 65 and the pinon gear 64 in the clockwise direction to drive the rack 62 downward. The claw 71a of the pawl prevents counter-clockwise rotation of the pinion gear, which thereby prevents upward vertical movement of the rack 62. Counter-clockwise rotation of the pinion gear 64, and thus upward movement of the rack 62, can be permitted by depressing the pawl 71 against the torsion spring 72 to release the claw from the ratchet gear 70. The thumbwheel knob 77 (FIGS. 12, 16) is mounted to the end of the pinion shaft 65 and can be manually rotated to rotate the pinion gear 64 in the counter-clockwise direction to raise the rack 62.

The ratchet gear 70, and thus the pinion shaft 65, are manually rotated in the clockwise direction (as shown in FIG. 11) by way of a handle 74 fastened to a handle mount 73, as shown in FIGS. 11-16. The handle mount 73 is pivotably supported on the pinion shaft 65, as best seen in FIG. 12, and the pawl 71 is fixed to the handle mount 73 so that the pawl can be rotated relative to the pinion shaft. However, when the claw 71a of the pawl is engaged to the ratchet gear 70, this rotation of the handle mount causes rotation of the ratchet gear 70 and thus rotation of the pinion shaft and pinion gear 64. In particular pushing the handle 74 downward toward the mounting plate 52 produces the clockwise rotation of the pinion gear 64, leading to the downward movement of the rack 62. In one specific embodiment, the handle 74 has a fulcrum length of 18-20 inches, which provides a leverage ratio of at least 27:1 between the force applied to push the handle down and the downward force applied by the vertical movement of the rack 62 when cutting through bone, as described in more detail herein. The pinion gear 64 can have an outer diameter of 1.375 inches with twelve gear teeth, while the rack can include 20 gear teeth configured to match the profile of the pinion gear teeth. The rack teeth thus span a length of 6.219 inches in the specific embodiment to thereby provide a rack travel distance of about six inches.

In accordance with this embodiment, the bone cutting assembly 50 is provided with an upper cutting assembly 80 and a lower cutting assembly 82 (FIGS. 10-11). The upper cutting assembly is configured to be moved toward the lower cutting assembly to cut a bone segment B positioned between the two assemblies, as shown in FIG. 10. The upper cutting assembly 80 includes an upper blade mounting plate 84 that is slidably mounted on two guide posts 86 that are themselves supported on the base 55. The plate 84 can include a pair of bushings 85 to slidably receive the posts, as best seen in FIG. 11. Each post includes concentrically mounted springs 87 disposed between the upper blade mounting plate 84 and the base 55. The springs 87 help ensure uniform movement of the upper blade mounting plate 84 toward the base and provides a return force to lift the plate after the cutting operation is completed. The upper blade mounting plate 84 is fastened to the bottom of the rack 62 by a mounting bolt 90 so that the plate moves with the rack. Thus, when the operator pushes the handle 74 downward, this force is transmitted through the pawl, ratchet gear, pinion gear and rack to move the upper blade mounting plate 84 downward against the upward force of the springs 87.

Figure 18:
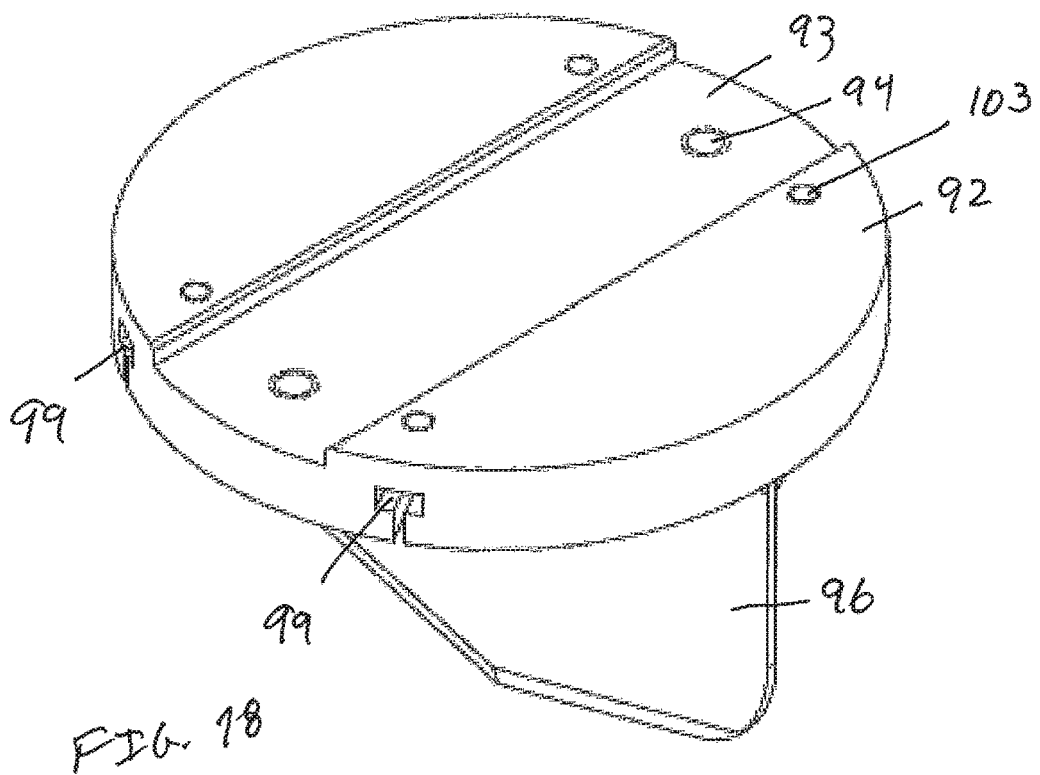
FIG. 18 is an enlarged side perspective view of an upper cutting element for use in the apparatus of FIG. 10.
Figure 19:
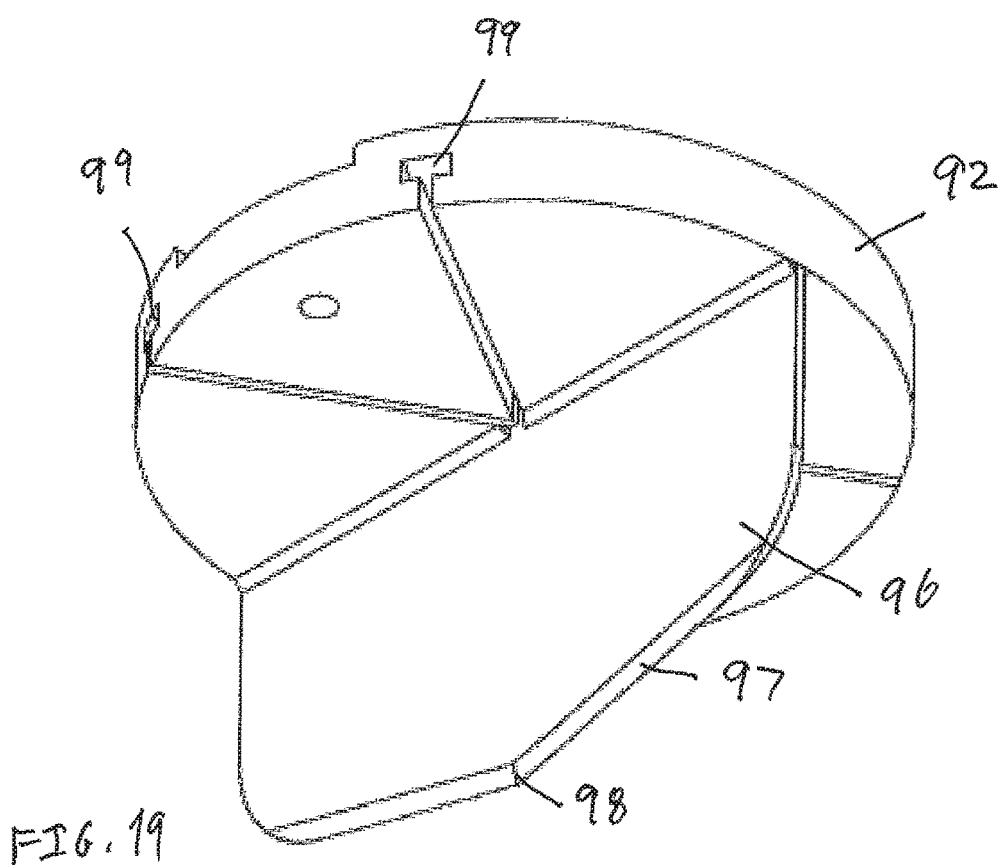
FIG. 19 is a bottom perspective view of the upper cutting element shown in FIG. 18.

The upper blade mounting plate 84 is configured to receive a removable and replaceable upper cutter base 92, as shown in FIGS. 11, 18, 19. The cutter base defines a channel 94 which receives the upper blade mounting plate 84 to fix the side-to-side position of the cutter base 92 relative to the mounting plate 84. Bolt holes 94 receive mounting bolts 95 (FIG. 11) that pass through aligned bolt holes in the mounting plate 84 to fasten the cutter base 92 to the mounting plate. It can thus be understood that different upper cutter bases may be provided with the bone cutting apparatus 50 of the present disclosure, each having the same channel 93 and bolt holes 94 for attachment to the upper blade mounting plate 84.

As shown in FIGS. 18, 19, the cutter base 92 includes a fixed blade 96 projecting from the underside of the cutter base. The fixed blade includes angled cutting edges 97 that converge to an apex 98 at the center of the cutter base 92 and that are configured to cut through bone. The cutter base 92 includes a plurality of T-shaped slots 99 extending radially from the center of the base to the outer perimeter of the base. The T-shaped slots are configured to receive replaceable cutter blades 88, shown in FIG. 20. The replaceable blades 88 include an upper rib 100 that is configured to be slidably received within a T-slot 99 of the cutter base 92. Each cutter blade 88 defines a cutting edge 101 configured to cut through bone. In the illustrated embodiment, the cutter blades 88 are configured so that the cutting edges 101 are angled upward toward the center of the cutter base, in contrast to the fixed blade 96 in which the cutting edges 97 are angled downward toward the center. Moreover, the cutting edges 101 of the replaceable blades 88 are offset upward from the apex 98 of the fixed cutter blade 96, as shown in FIG. 11. In a bone cutting operation, the fixed blade 96 contacts the bone segment first, followed by the replaceable blades 88 as the upper cutting assembly 80 is advanced downward toward the bone segment. It can be appreciated that the replaceable blades 88 can have cutting edges with different configurations from the cutting edge 101 shown in the illustrated embodiment. It can also be appreciated that different numbers of blades lots 99 can be provided in the upper cutter base 92 to receive different numbers of replaceable cutting blades 88. In the illustrated embodiment, four replaceable blades are provided along with the fixed blade 96 to provided six cutting edges 97, 101. The blade slots 99 in this embodiment are offset at 60° intervals, but other angular offsets are contemplated, including non-uniform angular offsets of the blades.

Figure 21:
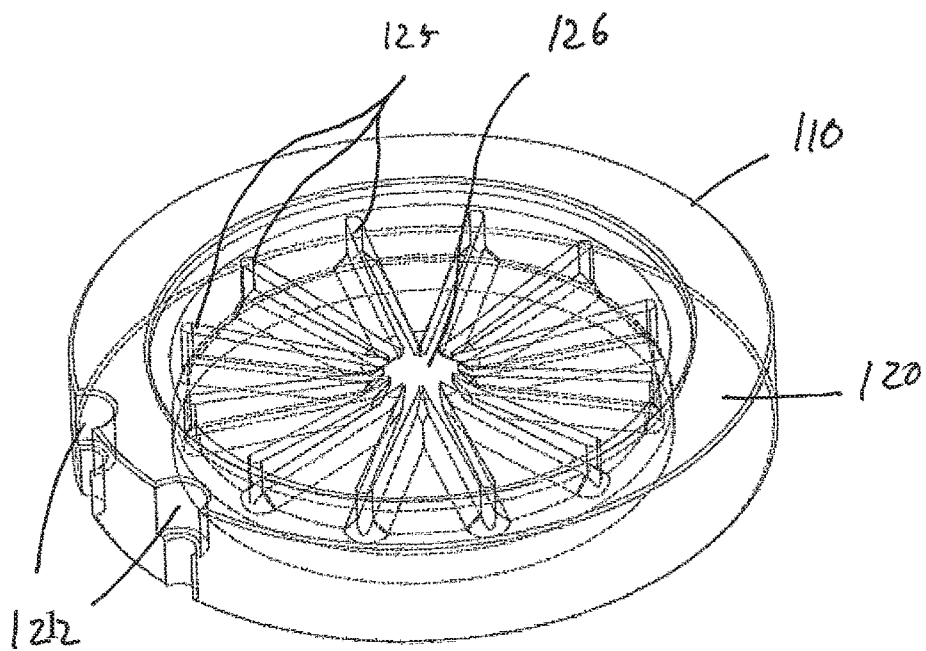
FIG. 21 is a perspective view of a bottom cutting tray for use in the apparatus shown in FIG. 10
Figure 22:
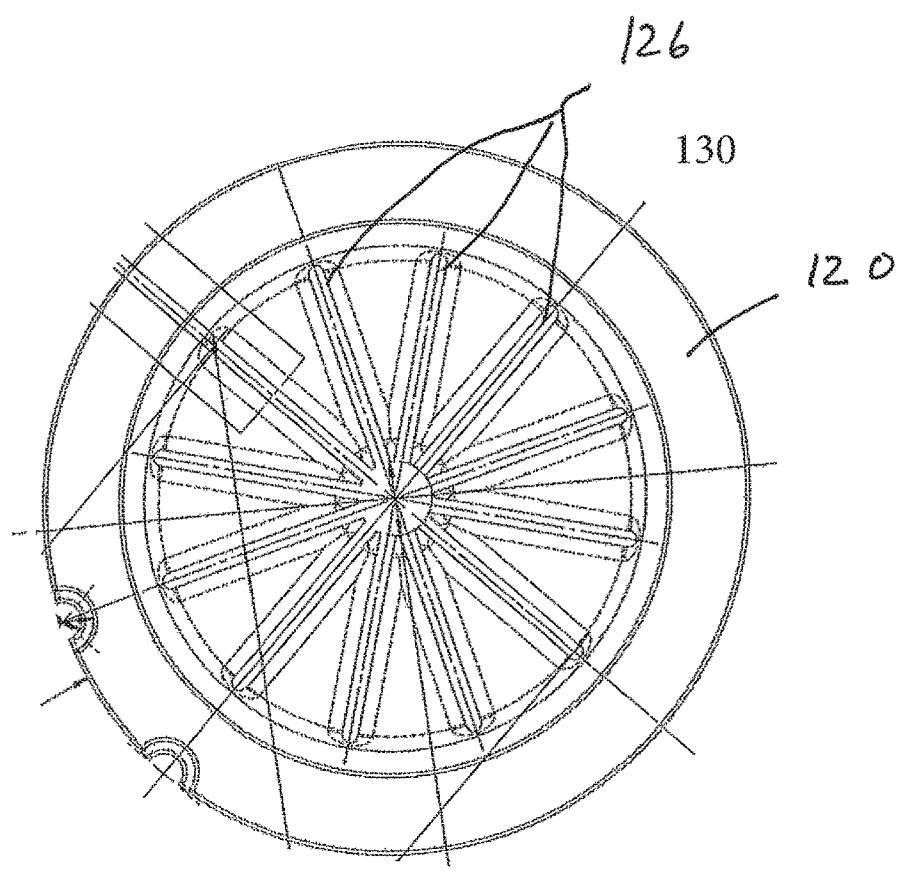
FIG. 22 is a top view of the bottom cutting tray shown in FIG. 21.
Figure 23:
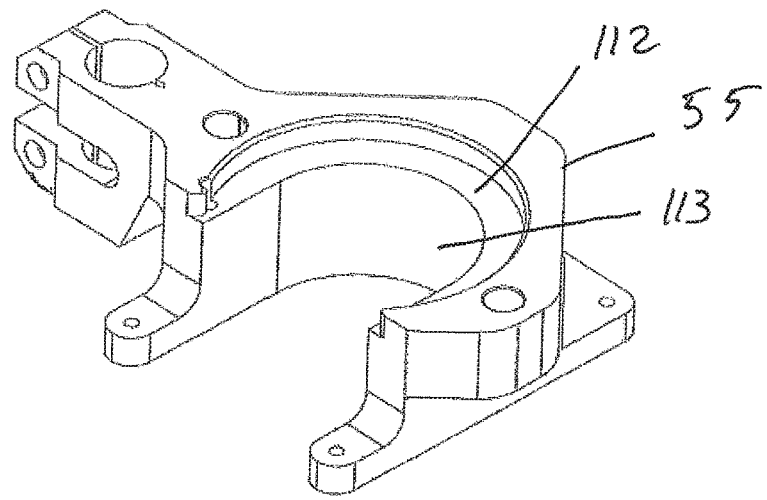
FIG. 23 is an enlarged perspective view of a base component of the apparatus shown in FIG. 10.
Figure 24:
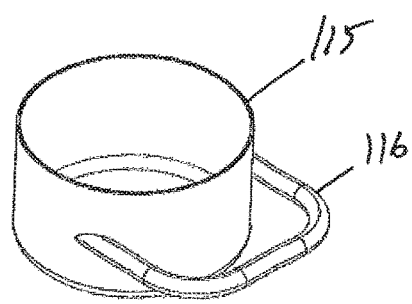
FIG. 24 is an enlarged perspective view of a collection container for use with the apparatus shown in FIG. 10.

The upper cutting assembly 80 is driven toward the lower cutting assembly 82 to cut a bone segment B positioned between the two assemblies. The lower cutting assembly includes a cutting tray 110 that is removably mounted in the base 55, as illustrated in FIG. 11. The base 55 defines aside opening cavity 113 with a ledge 112 for supporting the tray 110 above the cavity 113. The cavity is sized to receive a removable collection container 115 (FIG. 24) that can be placed below the tray and subsequently removed by a handle 116. As shown in FIG. 23, the ledge 112 more than 180°, and preferably about 240°, so that the cutting tray 110 is firmly retained within the base 55 during a cutting operation. The cutting tray 110 can include a circular rim 120 configured to be seated on the ledge 112. The rim 120 can define one or more alignment recesses 121 that are configured to receive an alignment post 122 fastened to the base 55 (FIGS. 10, 13). The alignment recesses and post fix the angular orientation of the cutting tray 110 relative to the upper cutting assembly 80 and upper cutting blades 88, 96. The cutting tray defines a plurality of slots 125 converging to a center opening 126, as shown in FIG. 21. The slots 125 are arranged to receive a corresponding cutting blade 88, 96 as the upper cutting assembly 80 is pushed through the bone segment B. The slots thus ensure that the blades pass completely through the bone segment to produce the requisite bone fragments. It can be appreciated that the number and angular arrangement of the slots 125 must coincide with the number and angular arrangement of the cutting blades of the upper cutting assembly 80. The cutting tray 110 defines a ledge 130 which supports a cutting guard 132 (FIGS. 10, 11). The cutting guard can be formed of a transparent material so that the cutting operation can be observed.

Figure 25:
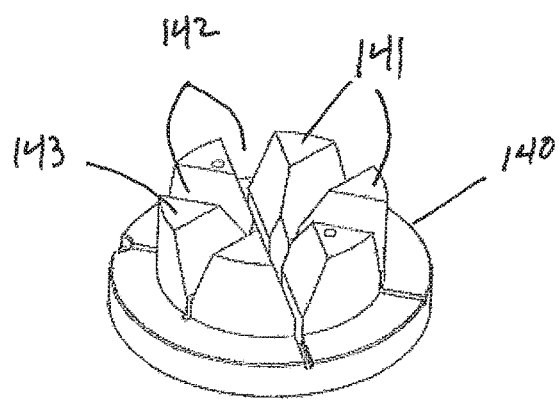
FIG. 25 is an enlarged perspective view of a blade assembly assist component for use with the apparatus shown in FIG. 10 and the upper cutting element and cutting blade shown in FIG. 18-20.

A blade assembly assist component 140 is provided for mounting the upper cutter base 92 to the blade mounting plate 84, as shown in FIG. 26. As shown in FIG. 25, the assist component 140 includes a plurality of bosses 141 that define blade slots 142 between the bosses. The bosses 141 further define support surfaces 144 on which the upper cutter base 92 is placed with the cutting blades 88, 96 extending into the slots 142. Alignment posts 104 (FIGS. 10, 26) are mounted in openings 103 in the cutter base 92 and are arranged to flank the sides of the upper blade mounting plate 84. The alignment posts 104 ensure that the bolts 95 in the mounting plate 84 are aligned with the bolt holes 94 in the upper cutter base 92. As shown in FIG. 26, the upper cutter base 92 with the full complement of cutting blades is placed on the blade assembly assist component 140 with the cutting blades facing downward into the slots 142. The assist component 140 is placed on the cutting tray 110 with the mounting face of the cutter base 92 facing the upper blade mounting plate 84. The handle 74 is pushed downward to move the mounting plate 84 downward toward the assist component 140 until the bolts 95 contact the bolt holes 94 in the cutter base 92. The bolts can then be tightened to draw the cutter base 92 into engagement with the mounting plate 84. The pawl 71 is then depressed to release the rack and pinion, and the knob 77 is rotated counter-clockwise in FIG. 11 to raise the rack 62 and thus the upper blade mounting plate 84 with the cutter base 92 and cutting blades 88, 96 mounted thereto. The blade assembly assist component 140 can then be removed from the cutting tray 110.

The bone cutting apparatus 50 can be used to cut a bone segment B into several fragments, even if the bone segment is frozen. The segment B is placed on the cutting tray 110 of the lower cutting assembly 82, as shown in FIG. 11. The bone segment is contained within the cutting guard 132. The upper cutting assembly 80 is outfitted with the desired cutting blades. As explained above, manually pushing the handle 74 downward drives the upper cutting assembly 80 downward toward the cutting tray 110. The cutting blades 88, 96 contact the bone segment and cut through the bone segment as the handle is pushed further downward. The mechanical advantage or leverage provided by the length of the handle 74 and the gear ratio between the rack 62 and pinion gear 64 allows a frozen bone segment to be cut into discrete fragments with only manual force. The ratchet gear 70 and pawl 71 arrangement allows the operator to push the handle down in intervals, rather than having to cut through the bone in a single motion. Once the cutting blades have passed through the bone segment, the pawl can be depressed to release the ratchet and thus the pinion gear 64. The springs 87 will push the upper blade mounting plate 84 upward somewhat, with the operator rotating the knob 77 to lift the rack 62 and upper cutting assembly 80 to its maximum upward position offset from the lower cutting assembly 82. The pawl 71 can be re-engaged to the ratchet gear 70 to hold the upper cutting assembly at this uppermost position ready for another bone cutting operation.

The cutting tray 110 can be configured so that the bone fragments fall into the collection container 115 positioned within the cavity 113 in the base 55 beneath the upper cutting assembly. For instance, the cutting tray can be configured like the base 47' shown in FIG. 9D in which pie-shaped opening are defined between the parts of the base forming the slots 47a' or receiving the upper cutting blades. Alternatively, the cutting tray 110 can be lifted from the base 55 and the bone fragments dumped into the collection container 115.

The bone cutting apparatuses 10, 50 are configured to cut through a bone segment, such as the bones of the pelvis, the long bones and vertebral bodies. The force required to cut through such bone is typically 800-900 lbf. The apparatuses of the present disclosure provide a force transmission mechanism from the user-operated handles 42, 74 to the upper cutting assemblies 20, 80. The force transmission mechanisms allow the typical operator to generate up to 1000 lbf by applying less than 50 lbf to the handle, which is well within the capability of most operators.

The present disclosure should be considered as illustrative and not restrictive in character. It is understood that only certain embodiments have been presented and that all changes, modifications and further applications that come within the spirit of the disclosure are desired to be protected.

What is claimed is:

1. A device for cutting a bone, comprising:
   a. a force transmission mechanism wherein said force transmission mechanism comprises an elongated force transducing member pivotally coupled to a gear mechanism, wherein said gear mechanism comprises a gear ratio configured to result in a generation of up to 1000 lbf when less than 50 lbf is applied to said elongated force transducing member;
   b. a manually operable handle coupled to an end of said elongated force transducing member, wherein said end is opposite of said gear mechanism; and
   c. a cutting element.

2. The device of claim 1, wherein said gear mechanism comprises a ratchet and a pawl gear assembly.

3. The device of claim 1, wherein said elongated force transducing member has a length of about 18 to about 20 inches providing a leverage ratio of at least 27:1 between a force exerted to push said handle and a force exerted by said elongated force transducing member.

4. The device of claim 1, wherein said bone is ex vivo.

5. The device of claim 1, wherein said cutting element is an upper cutting element or a lower cutting element.

6. The device of claim 5, wherein said upper cutting element or said lower cutting element comprises an alignment notch, wherein said alignment notch is specific to an additional cutting element.

7. The device of claim 5, wherein said upper cutting element, said lower cutting element, or both comprise one or more cutting blades wherein a cutting blade comprises one or more angles.

8. The device of claim 7, wherein said angles converge on an apex.

9. The device of claim 7, wherein said cutting blades are arranged in a radial pattern.

10. The device of claim 1, wherein said gear mechanism comprises a rack and a pinion wherein said pinion comprises a diameter of at least 1.375 inches and wherein said pinion comprises at least twelve gear teeth, and said rack comprises at least 20 gear teeth.

11. A device for cutting a bone, comprising:
    a. an elongated force transducing member;
    b. a linkage; and
    c. an upper cutting element,
       wherein said elongated force transducing member is coupled to said linkage and forms a first pivot with said linkage, wherein said linkage is coupled to said upper cutting element and forms a second pivot with said upper cutting element, and wherein said first pivot and said second pivot are offset; and
       wherein said offset is configured to result in a generation of up to 1000 lbf when less than 50 lbf is applied to said elongated force transducing member.

12. The device of claim 11, wherein said bone is ex vivo.

13. The device of claim 11, wherein said elongated force transducing member further comprises a ratchet and a pawl gear assembly.

14. The device of claim 11, wherein said elongated force transducing member has a length of about 18 to about 20 inches providing a leverage ratio of at least 27:1.

15. The device of claim 11, further comprising an upper cutting element and a lower cutting element.

16. The device of claim 15, wherein said lower cutting element comprises an alignment notch, wherein said alignment notch is specific to said upper cutting element.

17. The device of claim 15, wherein said upper cutting element, said lower cutting element, or both comprise one or more cutting blades wherein a cutting blade comprises one or more angles.

18. The device of claim 17, wherein said cutting blades are arranged in a radial pattern.

19. The device of claim 18, wherein said radial pattern comprises about a 60° angle formed between at least two cutting blades.

* * * * *

UNITED STATES PATENT AND TRADEMARK OFFICE
CERTIFICATE OF CORRECTION

| | |
|---|---|
| PATENT NO. | : 10,980,547 B2 |
| APPLICATION NO. | : 17/079309 |
| DATED | : April 20, 2021 |
| INVENTOR(S) | : Erik J. Woods, Brian H. Johnstone and Joseph Ingalls |

It is certified that error appears in the above-identified patent and that said Letters Patent is hereby corrected as shown below:

In the Specification

Column 1, Lines 14-17:
"This invention was made with government support under contract number HL142418 awarded by the National Heart, Lung and Blood Institute. The government has certain rights in the invention."
Should read:
-- This invention was made with government support under HL142418 awarded by the National Institutes of Health. The government has certain rights in the invention. --

Signed and Sealed this
Twenty-first Day of March, 2023

Katherine Kelly Vidal
*Director of the United States Patent and Trademark Office*